US00PP12581P2

(12) United States Plant Patent
Jauchen

(10) Patent No.: US PP12,581 P2
(45) Date of Patent: Apr. 30, 2002

(54) MINIATURE ROSE PLANT NAMED 'KORCROKIZA'

(75) Inventor: Daniel E. Jauchen, Santa Barbara, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 09/553,088

(22) Filed: Apr. 19, 2000

(51) Int. Cl.[7] ..... A01H 5/00
(52) U.S. Cl. ..... Plt./119
(58) Field of Search ..... Plt./119, 117, 116

*Primary Examiner*—Bruce R. Campell
*Assistant Examiner*—June Hwu
(74) *Attorney, Agent, or Firm*—Klarquist Sparkman LLP

(57) ABSTRACT

Miniature rose plant having a stable, cream flower color; ease of rooting from cuttings; rapid growth; good pot rose habit; and long shelf life.

1 Drawing Sheet

The present invention relates to a new and distinct variety of rose plant of the miniature class which was discovered as a single branch spontaneous flower color mutation on a rose plant of the variety 'KORprolit' (U.S. Plant Pat. No. 11,154) in a greenhouse in Santa Barbara, Calif.

'KORcrokiza' differs from 'KORprolit' principally in flower color. 'KORcrokiza' is a cream mutation of 'KORprolit', the flowers of which are light coral pink in color. Like 'KORprolit' 'KORcrokiza' is an ideal pot rose; easy to root from cuttings; grows rapidly; and has a good pot rose habit, long shelf life, and stable flower color.

Asexual reproduction of this new variety by cuttings, as performed at Somis and Santa Barbara, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) colour chart, except where ordinary dictionary significance of color is indicated.

Parentage: Spontaneous mutation of 'KORprolit' (U.S. Plant Pat. No. 11,154).

Classification:

*Botanical.*—*Rosa hybrida.*

*Commercial.*—Miniature rose.

FLOWER

Observations made from six-month old specimens grown in a greenhouse environment at Somis and Santa Barbara, Calif., January through November 1999.

Blooming habit: Continuous.

Bud:

*Size.*—¾ inch long when the petals start to unfurl.

*Form.*—The bud form is long; pointed ovoid.

*Color.*—When sepals first divide, bud color is Orange Group 27D. When half blown, the upper and lower sides of the petals are Orange Group 27D.

*Sepals.*—Color: Green Group 137D. Length: 1 3/16 inches–1 5/16 inches. Surface texture: Covered in fine hairs. There are three lightly appendaged sepals. There are two unappendaged sepals with hairy edges.

*Receptacle.*—Color: Green Group 137B. Shape: Funnel. Size: Small (about ¼ inch×3/16 inch). Surface: Smooth.

*Peduncle.*—Length: Short (about 1½ to 1¾ inches). Surface: Smooth with a few glands. Color: Green Group 137C with immature peduncles having a bronze cast of Greyed-Red Group 178B. Strength: Stiff; erect.

Bloom:

*Size.*—Small. Average open size is about 1¾ inches.

*Borne.*—Singly and several together in pyramidal clusters of three to five blooms.

*Stems.*—Strength Strong. Average length is about 5½ to 6 inches.

*Form.*—When first open: High centered. Permanence: Flattens; all petals curl.

*Petalage.*—Number of petals under normal conditions: 40 to 45.

*Color.*—The upper and reverse sides of the petals are Orange Group 27D. The base of each petal has a small, 1/16 inch×⅛ inch, Green-White Group 157D half moon at the point of attachment. The major color on the upper side is Orange Group 27D.

*Variegations.*—Occasional greenish white streak on the guard petals.

*Discoloration.*—The general tonality at the end of the first day: No change. At the end of the third day: No change. No change through day 16 to 18 when petal drop occurs.

*Fragrance.*—None.

Petals:

*Texture.*—Leathery.

*Shape.*—Broad obovate.

*Form.*—Tips slightly recurved; edges slightly quilled.

*Margin.*—Entire.

*Apex.*—Cuspidate.

*Base.*—Obtuse.

*Arrangement.*—Imbricated. Petaloids in the center are few (0 to 3 per flower); small (⅛ to ¼ inch long; 1/16 to ⅛ inch wide); and same color as petals.

*Persistence.*—Petals drop off cleanly before drying.

*Lastingness.*—On the plant: Very long (about 16 to 18 days). As a cut flower: Very long (about 20 days).

Reproductive parts:

*Stamens.*—Quantity: 100–120.

*Anthers.*—Size: Medium (1/16"–5/32"). Color: Yellow-Orange Group 18A. Arrangement: Regular around styles.

*Filaments.*—Color: Yellow Group 4C. Length: ⅛"–5/32".

*Pollen.*—Color: Not observed.

*Styles.*—Color: Green-White Group 157D. Length: 3/16"–¼".

*Stigmas.*—Color: Yellow-White Group 158C.

*Pistils.*—Quantity: 90–100.

*Hips.*—None observed.

Plant:

*Form.*—Bush.

*Growth.*—Vigorous; upright; branching. At maturity, height is 20 to 20 inches; width is 16 to 20 inches in a garden setting. In a 10 cm pot, height is 8 to 9 inches and width is 7 to 8 inches.

Foliage: Number of leaflets on normal mid-stem leaves: Five.

*Size.*—Small (2½ inches long×1¾inches wide).

*Quantity.*—Abundant.

*Color.*—New foliage: Upper and lower surfaces: Greyed-Red Group 178B. Old foliage: Upper surface: Green Group 139A. Lower surface: Green Group 139C.

Leaflets:

*Shape.*—Pointed oval.

*Texture.*—Leathery; glossy; upper and lower surfaces smooth with prominent veins on lower surface.

*Edge.*—Serrated.

*Serration.*—Single; small.

*Petiole rachis.*—Color: Greyed-Purple Group 183B. On new foliage has anthocyanin coloration, Greyed-Purple Group 184C.

*Petiole underside.*—Smooth with some glands.

*Stipules.*—Short (about ¼ inch); smooth; serrated. Color: Yellow-Green Group 146C.

*Disease resistance.*—Resistant to mildew under normal growing conditions. Not tested for blackspot and rust.

Wood:

*New wood.*—Color: Greyed-Red Group 178B. Bark: Smooth.

*Old wood.*—Color: Green Group 137C. Bark: Smooth.

Prickles:

*Quantity.*—On main canes from base: Few. On laterals from main canes: Few.

*Form.*—Short; hooked downward.

*Color when young.*—Greyed-Purple Group 183D.

*Color when mature.*—Greyed-Orange Group 174D.

*Size.*—1/32 inch.

Small prickles:

*Quantity.*—On main stalks: None. On laterals: None.

*Hardiness.*—Hardy to Zone 5.

Pest resistance: None observed.

I claim:

1. A new and distinct variety of rose plant of the miniature class, substantially as herein shown and described, characterized particularly by it's stable, cream flower color; ease of rooting from cuttings; rapid growth; good pot rose habit; and long shelf life.

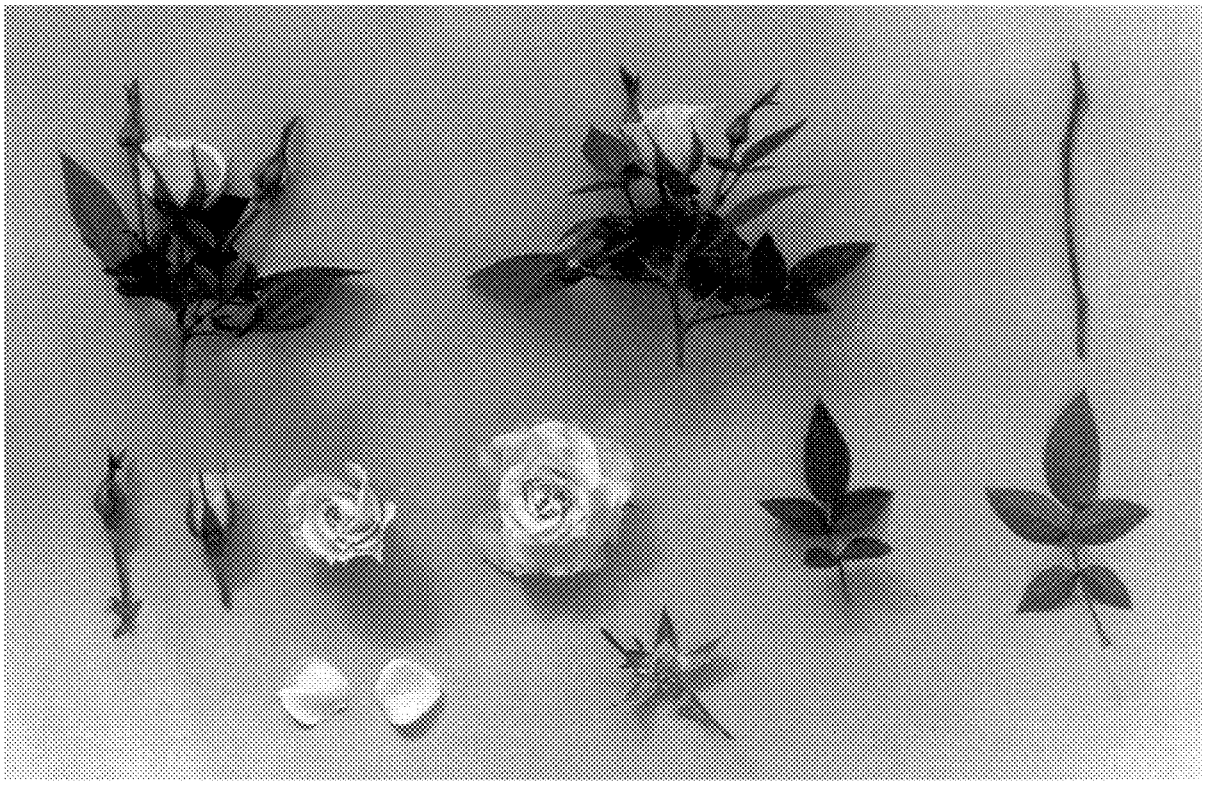

* * * * *